United States Patent
Ossenbach et al.

(10) Patent No.: US 10,343,967 B2
(45) Date of Patent: Jul. 9, 2019

(54) FUNCTIONALIZED PHOTOINITIATORS

(71) Applicant: SCHMID RHYNER AG, Adliswil (CH)

(72) Inventors: Alexander Ossenbach, Adliswil (CH); Dirk Schlatterbeck, Friltschen (CH); Peter Eladio Ludwig, Zurich (CH); Baktash Jahanbani, Niederrohrdorf (CH)

(73) Assignee: SCHMID RHYNER AG, Adliswil (CH)

( * ) Notice: Subject to any disclaimer, the term of this patent is extended or adjusted under 35 U.S.C. 154(b) by 0 days.

(21) Appl. No.: 15/564,429

(22) PCT Filed: Apr. 6, 2016

(86) PCT No.: PCT/EP2016/057548
§ 371 (c)(1),
(2) Date: Oct. 5, 2017

(87) PCT Pub. No.: WO2016/162389
PCT Pub. Date: Oct. 13, 2016

(65) Prior Publication Data
US 2018/0134645 A1    May 17, 2018

(30) Foreign Application Priority Data
Apr. 7, 2015  (CH) ........................ 0479/15

(51) Int. Cl.
| | | |
|---|---|---|
| *C07C 49/225* | (2006.01) | |
| *C07C 69/54* | (2006.01) | |
| *C07C 69/82* | (2006.01) | |
| *C07D 335/16* | (2006.01) | |
| *C07D 495/10* | (2006.01) | |
| *C09D 11/101* | (2014.01) | |
| *C09D 11/38* | (2014.01) | |
| *C09D 4/00* | (2006.01) | |
| *C08F 220/18* | (2006.01) | |
| *C08F 220/30* | (2006.01) | |

(52) U.S. Cl.
CPC ............ *C07C 49/225* (2013.01); *C07C 69/54* (2013.01); *C07C 69/82* (2013.01); *C07D 335/16* (2013.01); *C07D 495/10* (2013.01); *C08F 220/18* (2013.01); *C08F 220/30* (2013.01); *C09D 11/101* (2013.01); *C09D 11/38* (2013.01); *C08F 2220/305* (2013.01); *C09D 4/00* (2013.01)

(58) Field of Classification Search
CPC ....... C07C 49/225; C07C 69/82; C07C 69/54; C08F 220/30
See application file for complete search history.

(56) References Cited

U.S. PATENT DOCUMENTS

| | | |
|---|---|---|
| 2,675,367 A | 4/1954 | Caldwell |
| 5,527,925 A | 6/1996 | Chabrecek et al. |
| 2003/0215419 A1 | 11/2003 | Guire et al. |
| 2004/0249186 A1 | 12/2004 | Balzer et al. |
| 2005/0037277 A1* | 2/2005 | Herlihy ............... C07C 69/712 430/270.1 |
| 2005/0147919 A1 | 7/2005 | Kunz et al. |
| 2010/0049146 A1 | 2/2010 | Nielsen et al. |
| 2011/0063388 A1 | 3/2011 | Loccufier et al. |
| 2014/0335327 A1 | 11/2014 | Gevaert et al. |
| 2016/0225611 A1 | 8/2016 | Enomoto et al. |

FOREIGN PATENT DOCUMENTS

| | | | |
|---|---|---|---|
| CN | 101921184 A | 12/2010 | |
| DE | 10 2006 047 863 A1 | 4/2007 | |
| DE | 10 2012 216 170 A1 | 3/2014 | |
| DE | 102012216170 A1 * | 3/2014 | ............... C09D 4/00 |
| EP | 0 632 329 A1 | 1/1995 | |

(Continued)

OTHER PUBLICATIONS

Zaragoza Dorwald (Side Reactions in Organic Synthesis, 2005, WILEY-VCH Verlag GmbH & Co. KGaA, Weinheim, Preface. p. IX. (Year: 2005).*

(Continued)

Primary Examiner — Paul A Zucker
(74) Attorney, Agent, or Firm — Norman B. Thot

(57) ABSTRACT

The present invention provides mixtures of compounds and compounds having the formula:

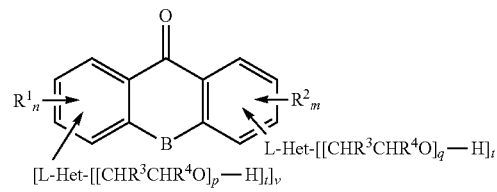

which are useful as functionalized photoinitiators and which may be used directly or after further functionalization in various photo-curable coating compositions, including varnishes, lacquers, printing inks and the like. The present invention also relates to a process to prepare the mixtures and the compounds. The present invention also provides radiation-curable surface coating compositions which include at least one of the compounds of the present invention as a photoinitiator. The compounds are especially suitable for radiation curable formulations which are intended for applications where low extracables or leachables are used such as printing inks for food packaging.

19 Claims, No Drawings

(56) References Cited

FOREIGN PATENT DOCUMENTS

| | | |
|---|---|---|
| EP | 2 130 817 A1 | 12/2009 |
| EP | 2 394 676 A1 | 12/2011 |
| EP | 2 617 705 A1 | 7/2013 |
| GB | 1193412 * | 1/1970 |
| WO | WO 99/47176 A2 | 9/1999 |
| WO | WO 03/033452 A1 | 4/2003 |
| WO | WO 03/064061 A1 | 8/2003 |
| WO | WO 2015/045426 A1 | 4/2015 |

OTHER PUBLICATIONS

Z. Wang et al.: "Process for preparation of multifunctional aromatic ketone compounds as photoinitiators", Chemical Abstracts Service, Abstract, p. 1 (2010).

* cited by examiner

FUNCTIONALIZED PHOTOINITIATORS

CROSS REFERENCE TO PRIOR APPLICATIONS

This application is a U.S. National Phase application under 35 U.S.C. § 371 of International Application No. PCT/EP2016/057548, filed on Apr. 6, 2016 and which claims benefit to Swiss Patent Application No. CH00479/15, filed on Apr. 7, 2015. The International Application was published in English on Oct. 13, 2016 as WO 2016/162389 A1 under PCT Article 21(2).

FIELD

The present invention relates to novel compounds which are useful as functionalized photoinitiators which may be used directly or, after further functionalization, in various photo-curable coating compositions including varnishes, lacquers, printing inks and the like, especially varnishes, as well as to a process to prepare such novel compounds. The present invention also provides radiation-curable surface coating compositions which include at least one of the compounds of the present invention as a photoinitiator.

BACKGROUND

Photoinitiators used in photo-curable compositions such as coating compositions need to provide good cure speed, low volatility, low yellowing, and good solubility, in particular in coating compositions. Increasing health awareness has furthermore led to lower legal limits in extractables, in particular where photocured coatings are likely to come or are intended to come into contact with food or food ingredients.

Another requirement for the photoinitiators to be useful in practice is that such compounds be accessable via efficient large scale processes and allow for easy processing and long term stability in coating compositions. For the latter, it is desired that the photoinitiators are low viscuous liquids which are highly compatible with other ingredients of photocurable compositions and thus do not give rise to flocculation or similar forms of deposit formation upon longer storage.

Benzophenone is known for its capability to provide fast curing, has a good solubility and shows a low degree of yellowing while being cheap and widely available. The drawbacks associated with its use, however, are an undesireable high degree of extractability and migration as well as its strong odor which prevents it from being used in modern packaging industry.

Another material that has an absorption maximum making it in principle useful as a photoinitiator is 4-hydroxybenzophenone. It is, however, rarely used for that purpose due to its poor solubility in UV curable formulations and its lower reactivity.

Several attempts were made to overcome these drawbacks by using functionalized benzophenones such as benzophenone-2-methyl ester (Speedcure MBB ex Lambson) and acrylated benzophenone (IRR261 ex UCB). Even though the aformentioned compounds are less volatile and thus cause less odor, their activity as photoinitiator is significantly lower compared to benzophenone.

Further known examples include benzophenone derivatives bound to a poly butandiol ether backbone via carboxymethoxy moities which are described in detail in WO 03/033452 A1 and are sold commercially as Omnipol BP.

The synthesis of these products starting from 4-hydroxybenzophenone requires several tedious reaction and isolation steps, thus rendering the overall efficiency low.

The products are also typically wax-like or highly viscous and thus hard to handle. Another disadvantage is that they still exhibit a substantial migration level when applied in coating compositions. Such products are also not compatible with photocurable compositions over the entire desired range and may form deposits upon longer storage.

Another attempt to overcome the problems of migration and odor was made by binding inter alia 4-benzophenonecarboxylic esters to a polymeric backbone bearing several hydroxy groups such as polyethylene glycol. Such compounds are, for example, disclosed in EP 2 394 676 A1 and are commercially available under the tradename Genopol* BP.

The disadvantages of these compounds are, however, that the carboxy substituted benzophenone derivatives have reduced reactivity.

EP 632 329 A and EP 2 617 705 disclose photoinitiators of the benzophenone, acetophenone or hydroxyacetophenone type which were functionalized with diisocyanates. Such products may be further functionalized with hydroxyalkyl(meth)acrylates to obtain photoiniitators which are capable of being incorporated into a polymer upon irradiation.

DE 10 2006 047 863 A discloses Photoinitiators inter alia of the hydroxy benzophenone type which are substituted by various ether functionalities.

WO03/064061 A discloses as two single compounds acrylic esters of ethoxylated 4-hydroxy-benzophenone with chain lengths of n=1 and n=4. The synthesis of such compounds is, however, according to own investigations, tedious and thus is not suitable to allow large scale and/or efficient manufacturing.

DE 102012216170 A discloses photoreactive polymers prepared from a monomer selected from (meth)acrylic esters of ethoxylated 2,5-dimethyl-4-hydroxy-benzophenone with chain lengths of 1 to 30, preferably 5 to 20.

The synthesis of monomers shown in Example 3 of DE 102012216170 A for n=9 proceeds via tosylation of the respective polyhydroxyethylacrylate and the coupling of the activated ester with 2,5-dimethyl-4-hydroxy-benzophenone, and is thus quite inefficient in terms of aiding agents.

The monomers as such were not employed as photoinitiators.

WO99/47176 A discloses a PEG200 ethoxylated 4-hydroxymethyl-benzophenone as starting material for further functionalisation. It is not used as photoinitiator.

SUMMARY

An aspect of the present invention was to provide improved photoinitiators having low odor, good reactivity, particularly good surface curing, a limited tendency to migrate and be extracted, and which does not yellow when cured. An aspect of the present invention is that such photoinitiators be easy to prepare, provide for an easy processing, and show high compatibility with typical ingredients of photocurable compositions.

DETAILED DESCRIPTION

In an embodiment, the present invention provides mixtures comprising compounds of formula (IV)

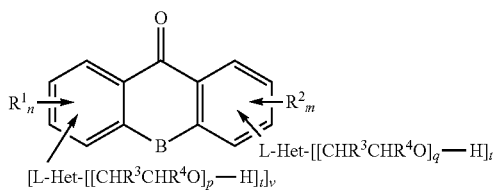

(IV)

wherein
the arrows denote substitution at the aromatic ring without specifically indicating the relative position to the depicted keto-group if not mentioned otherwise hereinafter, and wherein
B is either missing, and the two aromatic rings are then therefore substituted with hydrogen, or where n or m are not zero alternatively also with $R^1$ or $R^2$ respectively, at the position where B is depicted to be bound at the aromatic ring, or is
sulfur or oxygen,
whereby B can, for example, be missing or sulfur,
n is 0, 1 or 2, for example, 0 or 1, for example, 0,
$R^1$ is independently of other substituents $R^1$ which may be present selected from the group consisting of $C_1$-$C_{18}$-alkyl, $C_2$-$C_{18}$-alkenyl, $C_1$-$C_{18}$-alkoxy, $C_1$-$C_{18}$-alkylthio $C_6$-$C_{14}$-aryl, $C_6$-$C_{14}$-aryloxy, $C_6$-$C_{14}$-arylthio, —N($R^5$)$_2$, fluoro, chloro and COOR$^5$, with $R^5$ being hydrogen or $C_1$-$C_{18}$-alkyl,
m is 0, 1 or 2, for example, 0 or 1, for example, 0,
$R^2$ is independently of other substituents $R^2$ which may be present selected from the group consisting of $C_1$-$C_{18}$-alkyl, $C_2$-$C_{18}$-alkenyl, $C_1$-$C_{18}$-alkoxy, $C_1$-$C_{18}$-alkylthio, $C_6$-$C_{14}$-aryl, $C_6$-$C_{14}$-aryloxy, $C_6$-$C_{14}$-arylthio, —N($R^5$)$_2$, fluoro, chloro and COOR$^5$, with $R^5$ being hydrogen or $C_1$-$C_{18}$-alkyl, and
v is 0 or 1, for example, 0, and
the substituents L-Het[[CHR$^3$CHR$^4$O]$_p$—H]$_t$, if present, and L-Het-[CHR$^3$CHR$^4$O]$_q$—H]$_t$ independently of each other occupy the ortho-, meta or the para-position, for example, the ortho- or the para-position, for example, the para-position, at their respective aromatic ring and with respect to the keto-function depicted in formula (IV), and
wherein
L is independently missing or a methylene group, i.e., Het is either directly bound to the aromatic ring or via a methylene group,
Het is independently sulphur, oxygen, N($C_1$-$C_{18}$-Alkyl), or N, for example, oxygen,
t is 1 for Het=sulphur, oxygen, N($C_1$-$C_{18}$-Alkyl), and is 2 for Het=N,
$R^3$ and $R^4$ are either identically hydrogen or one of $R^3$ and $R^4$ is hydrogen and the other is methyl, whereby, in $R^3$ and $R^4$ are, for example, identically hydrogen, and
p and q independently of each other represent an integer of 0 or more, for example, 1 or more, for example, of from 1 to 20, for example, of from 1 to 10,
wherein with respect to the number of repeating units p and q, however,
at least 50 wt.-%, for example, at least 55 wt.-%, and, for example, at least 60 wt.-% of the total weight of compounds of formula (IV) within the mixture are those of formula (IV), wherein q, where v is 0 and t is 1, or
at least one of p and q, where both t are 1, or
at least one of all q, where v=0 and t is 2, or
at least one of all p and all q, where v=1 and where at least one t is 2,
is 3 or more, for example, 3 to 20, for example, 3 to 10, and, for example, 3, 4, 5, 6, 7 or 8,
wherein none of the single compounds of formula (IV) is present in an amount of more than 50 wt.-% with respect to the total weight of compounds of formula (IV) in the mixture,
or alternatively
wherein with respect to the number of repeating units p and q, however, at least 50 wt.-%, for example, at least 55 wt.-% and, for example, at least 60 wt.-% of the total weight of compounds of formula (IV) within the mixture are those of formula (IV), wherein
at least one of p and q where both t are 1 or of all p and all q where at least one t is 2,
is 3 or more, for example, 3 to 20, for example, 3 to 10, and, for example, 3, 4, 5, 6, 7 or 8, and wherein none of the single compounds of formula (IV) is present in an amount of more than 50 wt.-% with respect to the total weight of compounds of formula (IV).

The present invention also encompasses all combinations of the embodiments, ranges parameters as disclosed hereinafter either each other or the broadest disclosed range or parameter.

In an embodiment of the present invention, none of the single compounds of formula (IV) is present in an amount of more than 45 wt.-%, for example, not more than 40 wt.-%, with respect to the total weight of compounds of formula (IV) in the mixture.

In an embodiment of the present invention, the total amount of compounds of formula (IV) present in the mixture comprising compounds of formula (IV) having at least one of q or where present p and q being 5 or larger is 20 wt.-% or less, for example, 15 wt.-% or less, and, for example, 12 wt.-% or less.

The weight of compounds of formula (IV) with respect to the total weight of the mixture according to the present invention is from 10 to 100 wt.-%, for example, 80 to 100 wt.-%, for example, 90 to 100 wt.-% and, for example, 95 to 100% wt.-%.

The remainder to 100 wt.-%, if present, may, for example, comprise the respective ketals of compounds of formula (IV), i.e., compounds of formula (III), unreacted compounds of formula (II), and their ketals, solvents or catalyst residues.

In an embodiment of the present invention, the compounds of formula (IV) in the mixtures according to the present invention are those of formula (IVa)

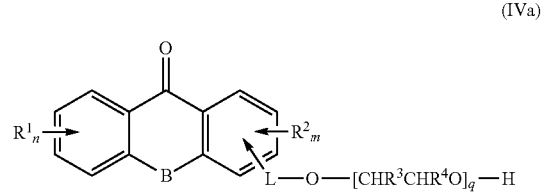

(IVa)

wherein the arrows, B, n, $R^1$, m, $R^2$, $R^3$, $R^4$ and L have the same meaning as set forth for formula (IV) above, and
q represents an integer of 0 or more, for example, 1 or more, for example, from 1 to 20, for example, from 1 to 10, wherein, with respect to the number of repeating units q, at least 50 wt.-%, for example, at least 55 wt.-% and, for example, at least 60 wt.-% of the total weight of compounds of formula (IVa) within the mixture are those of formula (IVa) having a number of repeating units q of 3 or more, for example, of 3 to 20, for example, 3 to 10, and, for example 3, 4, 5, 6, 7 or 8, and wherein none of the single compounds of formula (IVa) is present in an amount of more than 50 wt.-% with respect to the total weight of compounds of formula (IVa).

In an embodiment of the present invention, the total amount of compounds of formula (IVa) present in the mixture comprising compounds of formula (IVa) wherein q is 5 or larger can, for example, be 20 wt.-% or less, for example, 15 wt.-% or less, and, for example, 12 wt.-% or less.

In an embodiment of the present invention, none of the single compounds of formula (IVa) is, for example, present in an amount of more than 45 wt.-%, for example, not more than 40 wt.-% with respect to the total weight of compounds of formula (IVa) in the mixture.

The weight of compounds of formula (IVa) with respect to the total weight of the mixture according to the present invention is from 10 to 100 wt.-%, for example, 80 to 100 wt.-%, for example, 90 to 100 wt.-% and, for example, 95 to 100% wt. %.

The remainder to 100 wt.-%, if present, may, for example, comprise the respective ketals of compounds of formula (IVa) and catalyst residues.

In an embodiment of the present invention, the compounds of formula (IV) in the mixtures according to the present invention are those of formula (IVb)

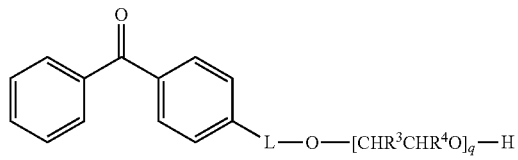

wherein L, $R^3$ and $R^4$ have the meaning set forth above for formula (IV), and q represents an integer of 0 or more, for example, 1 or more, for example, from 1 to 20, for example, from 1 to 10, wherein, with respect to the number of repeating units q, at least 50 wt.-%, for example, at least 55 wt.-% and, for example, at least 60 wt.-% of the total weight of compounds of formula (IVb) within the mixture are those of formula (IVb) having a number of repeating units q of 3 or more, for example, of 3 to 20, for example, 3 to 10 and, for example, 3, 4, 5, 6, 7 or 8, and wherein none of the single compounds of formula (IVb) is present in an amount of more than 50 wt.-% with respect to the total weight of compounds of formula (IVb).

In an embodiment of the present invention, the total amount of compounds of formula (IVb) present in the mixture comprising compounds of formula (IVa) wherein q is 5 or larger can, for example, be 20 wt.-% or less, for example, 15 wt.-% or less, and, for example, 12 wt.-% or less.

In an embodiment of the present invention, none of the single compounds of formula (IVb) is, for example, present in an amount of more than 45 wt.-%, for example, not more than 40 wt.-% with respect to the total weight of compounds of formula (IVb).

In an embodiment of the present invention L is missing.

The present invention further relates to compounds of formula (I) that can form part of mixtures of compounds of formula (IV), (IVa) or (IVb)

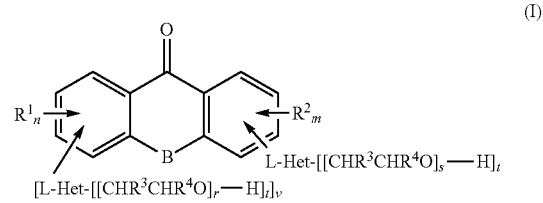

wherein the arrows, B, n, $R^1$, m, $R^2$, $R^3$ and $R^4$, v, L, Het and t have the same meaning as set forth for formula (IV) above, and the substituents L-Het[[CHR$^3$CHR$^4$O]$_r$—H]$_t$, if present, and L-Het-[CHR$^3$CHR$^4$O]$_s$—H]$_t$ independently of each other occupy the ortho-, meta or the para-position, for example, the ortho- or the para-position and, for example, the para-position at their respective aromatic ring and with respect to the keto-function depicted in formula (I), and if t is 1 for both substituents L-Het[[CHR$^3$CHR$^4$O]$_r$—H]$_t$ and L-Het-[CHR$^3$CHR$^4$O]$_s$—H]$_t$, either r or s is an integer of 3 or more, for example, from 3 to 20, for example, from 3 to 10, and, for example, 3, 4, 5, 6, 7 or 8, and the respective other of r or s is an integer of 1 or more, for example, from 1 to 20, for example, of from 1 to 10 and, for example, 3, 4, 5, 6, 7, 8 or 9, for example, 3, or if t is 2 for one or both substituents L-Het[[CHR$^3$CHR$^4$O]$_r$—H]$_t$ and L-Het-[CHR$^3$CHR$^4$O]$_s$—H]t, at least one r or s is an integer of 3 or more, for example, from 3 to 20, for example, from 3 to 10 and, for example, 3, 4, 5, 6, 7 or 8, and the other residues r and/or s are an integer of 1 or more, for example, from 1 to 20, for example, from 1 to 10 and, for example, 3, 4, 5, 6, 7, 8 or 9, for example, 3. In an embodiment, t is r and s are independently of one another an integer of 3 or more, for example, from 3 to 20, for example, from 3 to 10 and, for example, for example, 5, 6, 7 or 8 or 3.

As used herein, and unless specifically stated otherwise, $C_1$-$C_{18}$-alkyl, $C_1$-$C_{18}$-alkoxy and $C_1$-$C_{18}$-alkylthio, include straight-chained or, for $C_3$-$C_{18}$ also cyclic either in part or as a whole, branched or unbranched alkyl, alkoxy and alkylthio substituents having the given number of carbon atoms in the substituent as such.

As used herein, and unless specifically stated otherwise, $C_2$-$C_{18}$-alkenyl include straight-chained or, for $C_5$-$C_{18}$ also cyclic either in part or as a whole, branched or unbranched alkenyl, having the given number of carbon atoms in the substituent as such.

As used herein, and unless specifically stated otherwise, $C_6$-$C_{14}$-aryl, $C_6$-$C_{14}$-aryloxy and $C_6$-$C_{14}$-arylthio denote carbocyclic aromatic substituents having six to fourteen carbon atoms within the aromatic system as such, i.e., without carbon atoms of substituents, for example, phenyl ($C_6$), naphthyl ($C_{10}$), phenanthrenyl and anthracenyl (each $C_{14}$), whereby said carbocyclic, aromatic substituents are either unsubstituted or substituted by up to five identical or different substituents per cycle. For example, the substituents are selected from the group consisting of fluoro, chloro, $C_1$-$C_{18}$-alkyl, $C_1$-$C_{18}$-alkoxy, $C_6$-$C_{14}$-aryl.

In an embodiment of the present invention, the carbocyclic, aromatic substituents can, for example, be unsubstituted.

Specific examples of $C_1$-$C_{18}$-alkyl are methyl, ethyl, n-propyl, isopropyl, n-butyl, sec-butyl, tert-butyl, n-pentyl, isopentyl, tert.-pentyl, neopentyl, cyclohexyl, n-hexyl, n-heptyl, n-octyl and isooctyl, n-decyl, n-dodecyl n-hexadecyl, n-octadecyl.

Specific examples of $C_1$-$C_{18}$-alkoxy-substituents are methoxy, ethoxy, isopropoxy, n-propoxy, n-butoxy, sec.-butoxy, tert-butoxy and cyclohexyloxy.

Specific examples of $C_1$-$C_{18}$-alkylthio-substituents are methylthio abnd ethylthio.

Specific examples of $C_6$-$C_{14}$-aryl are phenyl, o-, m- and p-tolyl.

A specific example of an $C_6$-$C_{14}$-aryl-substituent is phenoxy.

A specific example of an $C_6$-$C_{14}$-aryl-substituent is phenylthio.

In an embodiment of the present invention,
n is 0 or 1,
$R^1$ is independently of other substituents $R^1$ which may be present selected from the group consisting of $C_1$-$C_{18}$-alkyl, $C_1$-$C_{18}$-alkoxy, $C_6$-$C_{14}$-aryl and chloro,
m is 0 or 1,
$R^2$ is independently of other substituents $R^2$ which may be present selected from the group consisting of $C_1$-$C_{18}$-alkyl, $C_1$-$C_{18}$-alkoxy, $C_6$-$C_{14}$-aryl and chloro.

In an embodiment of the present invention, n and m are 0.

An example of compounds of formula (I) are those of formula (Ia)

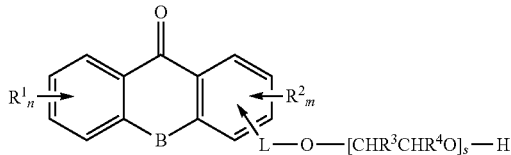

(Ia)

wherein the arrows, B, $R^1$, n, $R^2$, m, $R^3$ and $R^4$, L have the meaning set forth above for formula (I), and
s is an integer of 3 or more, for example, of from 3 to 20, for example, of from 3 to 10 and, for example, represents 5, 6, 7 or 8.

In an embodiment in formula (Ia),
the arrow for L-O—[$CHR^3$—$CHR^4$—O]$_s$—H denotes substitution at the ortho- or para position, for example, at the para position at the aromatic ring relative to the depicted keto-group, and
B is missing,
n and m are 0,
L is missing,
$R^3$ and $R^4$ are either identically hydrogen or one of $R^3$ and $R^4$ is hydrogen and the other is methyl, whereby, in $R^3$ and $R^4$ can, for example, be identically hydrogen, and
s is an integer of 3 or more, for example, from 3 to 20, for example, from 3 to 10 and, for example, represents 5, 6, 7 or 8 or 3.

An example of compounds of formula (I) are those of formula (Ib)

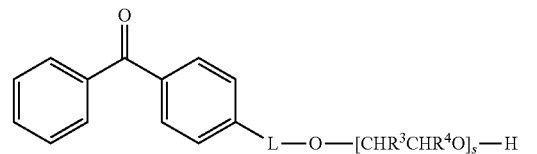

(Ib)

wherein L, $R^3$ and $R^4$ and s have the meaning set forth above for formula (I) and formula (Ia).

The compounds of formula (I) or the mixtures of compounds of formula (IV) may be prepared by a process comprising at least the step of reacting one or more compounds, for example, one compound of formula (II)

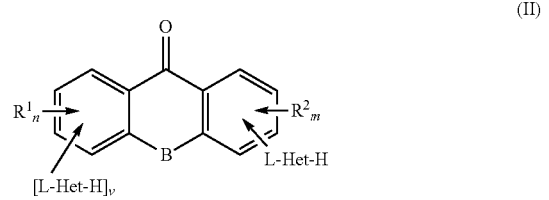

(II)

wherein the arrows, B, $R^1$, n, $R^2$, m, v, L and Het have the meaning set forth for formulae (I) and (IV) above,
with ethylene oxide and/or propylene oxide in the presence of a catalyst or in the absence of a catalyst.

Compounds of formulae (Ia) and (IVa) are accordingly accessible from compounds of formula (IIa)

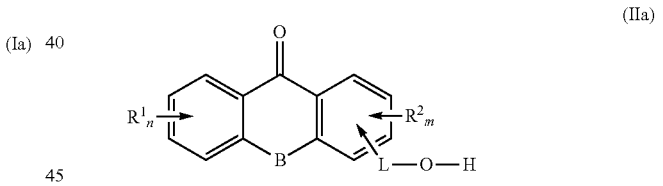

(IIa)

wherein the arrows, B, $R^1$, n, $R^2$, m and L have the meaning set forth for formulae (Ia) and (IVa) above.

Compounds of formulae (Ib) and (IVb) are accordingly accessible from 4-hydroxybenzophenone and 4-hydroxymethylbenzophenone. Specific starting materials of formula (II) include 2-hydroxythioxanthen-9-one, 4,4'-dihydroxybenzophenone, 4-hydroxybenzophenone, and 4-hydroxymethylbenzophenone.

The process according to the present invention may be carried out as a continuous or as a batch process.

In an embodiment of the present invention, ethylene oxide can, for example, be used. In another embodiment, propylene oxide can, for example, be used. In another embodiment, a mixture of ethylene oxide and propylene oxide can, for example, be used.

In an embodiment of the present invention, ethylene oxide can, for example, be used.

The molar ratio of ethylene oxide, propylene oxide or the sum thereof to the compound(s) of formula (II) depends on the desired number of repeating units (p, q, r, s). To, for example, obtain compounds of formula (I) or mixtures of compounds according to formula (IV) in a sufficient amount, the above molar ratio should be at least 2.5, for example, at least 3, for example, at least 3.5 per substituent L-Het-H if Het is oxygen, sulphur or $N(C_1-C_{18}$-Alkyl) or the respective double amounts per substituent if Het is N.

In an embodiment of the present invention, the molar ratio of ethylene oxide, propylene oxide or the sum thereof to the compound(s) of formula (II) can, for example, be from (r+s)+0.01 to (r+s)+1.0, for example, (r+s)+0.1 to (r+s)+1.0, wherein r and s are the desired number of repeating units and whereby (r+s) refers to the sum of all repeating units bound to Het in the molecule of formula (I).

Accordingly, where compounds of formula (IIa) are used as starting material, the molar ratio of ethylene oxide, propylene oxide or the sum thereof to the compound(s) of formula (IIa) is from s+0.01 to s+1.0, for example, from s+0.1 to s+1.0, wherein s is the desired number of repeating units.

Analogously, in an embodiment of the present invention, the molar ratio of ethylene oxide, propylene oxide or the sum thereof to the compound(s) of formula (II) can, for example, be from (p+q)+0.01 to (p+q)+1.0, for example, from (p+q)+0.1 to (p+q)+1.0, wherein p and q are the desired number of repeating units and whereby (p+q) refers to the sum of all repeating units bound to Het in the molecules of formula (IV).

Accordingly, where compounds of formula (IIa) are used as starting material, the molar ratio of ethylene oxide, propylene oxide or the sum thereof to the compound(s) of formula (IIa) is from q+0.01 to q+1.0, for example, from q+0.1 to q+1.0, wherein q is the desired number of repeating units.

In an embodiment of the present invention, the process is effected using a flow-through reactors, stirred tank reactors, tubular reactor, gas-liquid stirred reactors, Venturi-loop reactors or spray tower loop reactors.

In an embodiment of the present invention, the process can, for example, be carried out at a temperature in the range of 20° C. to 200° C., for example, in the range of 60° C. to 180° C. and, for example, in the range of 80° C. to 150° C.

The reaction pressure is typically from 500 to 200,000 hP, for example, from 1,000 to 100,000 hPa, for example, from 1,500 to 50,000 hPa and, for example, from 2,000 to 30,000 hPa.

The process according to the present invention is either carried out in an organic diluent or without organic diluent, whereby organic diluent is meant to be an organic compound which is liquid at 25° C. which does virtually not react with ethylene oxide or propylene oxide at temperatures of up to 200° C.

In particular where no organic diluent is employed, the process can, for example, be carried out above the melting point of the compound of formula (II) or the employed mixture of compounds of formula (II).

Suitable diluents, where desired, include aliphatic hydrocarbons or any mixture thereof such isoaliphatic hydrocarbons according to CAS 64741-65-7, in particular aliphatic hydrocarbons including hydrocarbons such as methycyclopentane, 2-methylpentane, 3-methylpentane, n-hexane, and cyclohexane, aromatic hydrocarbons such as benzene, toluene, xylene, ortho-xylene, para-xylene and meta-xylene, and ethers such as 1,4-dioxane.

In an embodiment of the present invention, the reaction time can, for example, be from 2 min to 24 h, for example, from 10 min to 16 h and, for example, from 3 to 12 h.

The process may be carried out batchwise or continuously. Where a continuous reaction is performed, the reaction time given above represents the average residence time.

The reaction is either carried out in the presence of a catalyst or not.

In an embodiment, no catalyst added.

In an embodiment, a catalyst is added.

Catalysts may be acidic or basic, for example, basic. Examples of acidic catalysts include Brönsted acids and Lewis acids and may be either inorganic or organic. Specific examples of Brönsted acids include sulfuric acid, hydrochloric or phosphoric acid, a sulphonic acid, such as p-toluenesulphonic acid or methanesulphonic acid;

Specific examples of Lewis acid include aluminium chloride, boron trifluoride or an organotitanate.

Examples of basic catalysts include sodium or potassium hydroxide.

Byproducts that may be formed during the process according to the present invention are compounds of formula (III)

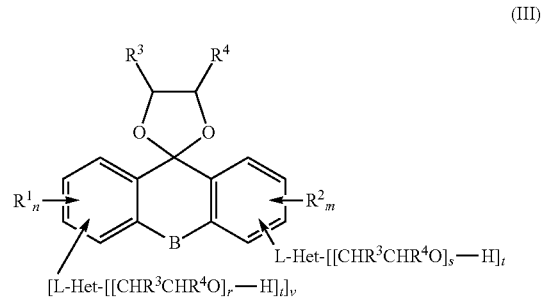

(III)

wherein the arrows, B, $R^1$, n, $R^2$, m, $R^3$, $R^4$, L, Het, v, t, r and s have the meaning set forth for formula (I) above and wherein s denotes q and r denotes p where mixtures of compounds of formula (IV) are concerned.

Since they are typically formed in a minor amount compared to their non ketalized analogoues of formula (I) and (IV), respectively, removal is typically not required to fulfil the intended purpose. In the event pure compounds of formula (I) are desired, the ketals may be removed by reacting the compounds of formula (III) with an acid in the presence of water.

As a potential starting material for compounds of formulae (I) and (IV), the compounds of formula (III) are also encompassed by the present invention.

In strict analogy, compounds of formula (IIIa) are formed as byproducts during the process according to the present invention to prepare compounds of formulae (Ia) and (IVa) starting from compounds of formula (IIa)

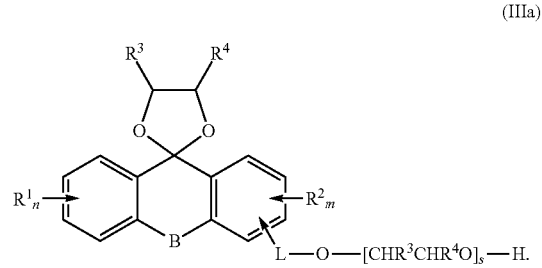

(IIIa)

In formula (IIIa), the arrows, B, $R^1$, n, $R^2$, m, $R^3$, $R^4$, s and L have the meaning including set forth for formula (Ia) above and wherein s denotes q where mixtures of compounds of formula (IVa) are concerned.

It is known to those skilled in the art that when the compounds of formula (I) are prepared according to the process described above, mixtures of several compounds are provided in which the number of repeating units of the ethylene oxide and/or propylene oxide moieties differs (mixtures of compounds of formula IV).

Isolation of pure compounds of formula (I) may be effected by chromatographic methods such as flash chromatography, preparative HPLC, and simulated moving bed chromatography.

However, it was found that the mixtures of compounds of formula (IV) require a lack of workup and purification steps while providing the same advantages as compounds of formula (I), but also provide further advantages, i.e., lower viscosity, and thus even better processing in combination therewith.

It was found that the compounds of formula (I) or mixtures comprising compounds of formula (IV) may further be functionalized.

The present invention therefore further encompasses compounds of formula (VI)

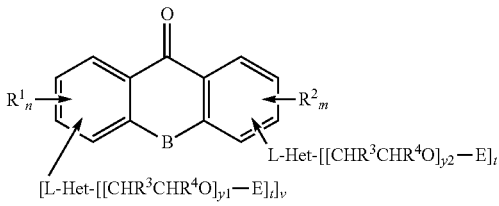

(VI)

wherein the arrows denote substitution at the aromatic ring without specifically indicating the relative position to the depicted keto-group if not mentioned otherwise hereinafter, and wherein B is either missing and the two aromatic rings are then therefore substituted with hydrogen, or where n or m are not zero, alternatively also with $R^1$ or $R^2$ respectively, at the position where B is depicted to be bound at the aromatic ring, or is sulfur or oxygen, whereby B can, for example, be missing or sulfur, n is 0, 1 or 2, for example, 0 or 1 and, for example, 0, $R^1$ is independently of other substituents $R^1$ which may be present selected from the group consisting of hydrogen, $C_1$-$C_{18}$-alkyl, $C_2$-$C_{18}$-alkenyl, $C_1$-$C_{18}$-alkoxy, $C_1$-$C_{18}$-alkylthio $C_6$-$C_{14}$-aryl, $C_6$-$C_{14}$-aryloxy, $C_6$-$C_{14}$-arylthio, —$N(R^5)_2$, fluoro, chloro and $COOR^5$ with $R^5$ being hydrogen or $C_1$-$C_{18}$-alkyl, m is 0, 1 or 2, for example, 0 or 1 and, for example, 0, $R^2$ is independently of other substituents $R^2$ which may be present selected from the group consisting of hydrogen, $C_1$-$C_{18}$-alkyl, $C_2$-$C_{18}$-alkenyl, $C_1$-$C_{18}$-alkoxy, $C_1$-$C_{18}$-alkylthio, $C_6$-$C_{14}$-aryl, $C_6$-$C_{14}$-aryloxy, $C_6$-$C_{14}$-arylthio, —$N(R^5)_2$, fluoro, chloro and $COOR^5$, with $R^5$ being hydrogen or $C_1$-$C_{18}$-alkyl, and wherein v is 0 or 1, for example, 0, the substituents L-Het-[[$CHR^3CHR^4O$]$_y$-E], where present, and L-Het-[[$CHR^3CHR^4O$]$_{y2}$-E] independently of each other occupy the ortho-, meta or the para-position, for example, the ortho- or the para-position and, for example, the para-position at their respective aromatic ring and with respect to the keto-function depicted in formula (I), and wherein L is independently missing or a methylene group, i.e., Het is either directly bound to the aromatic ring or via a methylene group, Het is independently sulphur, oxygen, $N(C_1$-$C_{18}$-Alkyl), NH or N, for example, oxygen, t is 1 for Het=sulphur, oxygen, $N(C_1$-$C_{18}$-Alkyl), NH, and is 2 for Het=N, $R^3$ and $R^4$ are either identically hydrogen or one of $R^3$ and $R^4$ is hydrogen and the other is methyl, whereby, for example, $R^3$ and $R^4$ are identically hydrogen, and if t is 1 y1 and y2 independently of each other represent an integer of 0 or more, for example, 1 or more, for example, from 1 to 20, for example, from 1 to 10 and, for example, 3 to 10, whereby the sum of y1 and y2 is at least 1 for v=1, or y2 is at least 1 where v=0, if t is 2 all y1 and y2 independently of each other represent an integer of 0 or more, for example, 1 or more, for example, from 1 to 20, for example, from 1 to 10 and, for example, 3 to 10, whereby the sum of all y1 and all y2 is at least 1 for v=1, or the sum of all y2 is at least 1 where v=0, and E independently, for example, identically represents $H_2C$=CH—CO—, ($CH_3$)HC=CH—CO— or $H_2C$=C($CH_3$)—CO—, for example, $H_2C$=CH—CO— and $H_2C$=C($CH_3$)—CO—, for example, $H_2C$=CH—CO—.

The preparation of compounds of formula (VI) may be effected by standard esterification procedures known to those skilled in the art, which include, for example, and as an exemplary embodiment contacting the compounds of formula (I) or mixtures of compounds of formula (IV) with acids E-H in the presence of an acid such as a mineral acid such as sulfuric or hydrochloric acid or a organic sulfonic acid such as p-toluene sulfonic acid and removing water e.g. via distillation. Alternatively, compounds of formula (I) or mixtures of compounds of formula (IV) can be treated with acid halides E-Hal, with Hal being Cl or Br, in the presence of a base such as an amine.

Compounds of formula (VI) are, for example, those of formula (VIa)

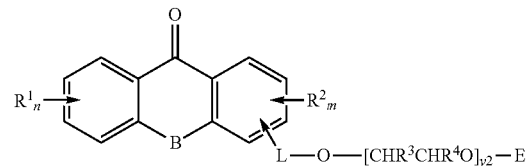

(VIa)

wherein the arrows, B, $R^1$, n, $R^2$, m, L, $R^3$, $R^4$ and E have the meaning set forth above for formula (VI) and y2 represents an integer of 1 or more, for example, 1 to 20, for example, 2 to 10, and, for example, 2, 3, 4, 5 or 6.

Compounds of formula (VI) can, for example, be compounds of formula (VIb)

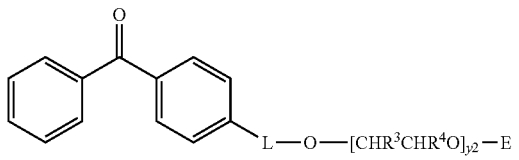

(VIb)

wherein L, $R^3$ and $R^4$ have the meaning set forth above for formula (VI), y2 represents an integer of 1 or more, for example, 1 to 20, for example, 2 to 10, and, for example, 2, 3, 4, 5 or 6, and E represents $H_2C=CH—CO—$ or $H_2C=C(CH_3)—CO—$, for example, $H_2C=CH—CO—$.

In an embodiment of the present invention, L can, for example, be missing.

The present invention further encompasses mixtures comprising compounds of formula (VI), wherein, with respect to the number of repeating units y1 and y2, at least 50 wt.-%, for example, at least 55 wt.-% and, for example, at least 60 wt.-% of the total weight of compounds of formula (VI) within the mixture are those of formula (VI), wherein y2, where v is 0 and t is 1, or at least one of y1 and y2, where both t are 1, or at least one of all y2, where v=0 and t is 2, or at least one of all y1 and all y2, where v=1 and where at least one t is 2, is 3 or more, for example, of 3 to 20, for example, 3 to 10, and, for example, 3, 4, 5, 6, 7 or 8, and wherein none of the single compounds of formula (VI) is present in an amount of more than 50 wt.-% with respect to the total weight of compounds of formula (VI) in the mixture, or alternatively wherein with respect to the number of repeating units y1 and y2 at least 50 wt.-%, for example, at least 55 wt.-% and, for example, at least 60 wt.-% of the total weight of compounds of formula (VI) within the mixture are those of formula (VI), wherein at least one of y1 and y2 where both t are 1 or of all p and all q where at least one t is 2, is 3 or more, for example, of 3 to 20, for example, 3 to 10 and, for example, 3, 4, 5, 6, 7 or 8, and wherein none of the single compounds of formula (VI) is present in an amount of more than 50 wt.-% with respect to the total weight of compounds of formula (VI).

In an embodiment of the present invention, none of the single compounds of formula (VI) can, for example, be present in an amount of more than 45 wt.-%, for example, not more than 40 wt.-%, with respect to the total weight of compounds of formula (VI).

In an embodiment, the present invention further encompasses mixtures comprising compounds of formula (VIa), for example, compounds of formula (VIb), wherein with respect to the number of repeating units y2, at least 50 wt.-%, for example, at least 55 wt.-% and, for example, at least 60 wt.-% of the total weight of compounds of formula (VIa) respectively formula (VIb) within the mixture are those of formula (VIa) respectively formula (VIb) having a number of repeating units y2 of 3 or more, for example, of 3 to 20, for example, 3 to 10 and, for example, 3, 4, 5, 6, 7 or 8, and wherein none of the single compounds of formula (VIa) resp. (VIb) is present in an amount of more than 50 wt.-% with respect to the total weight of compounds of formula (VIa) resp. (VIb).

In an embodiment of the present invention, the total amount of compounds of formula (IVa) respectively (VIb) present in the mixtures can, for example, comprise compounds of formula (IVa) wherein q is 5 or larger is 20 wt.-% or less, for example, 15 wt.-% or less, and, for example, 12 wt.-% or less.

The weight of compounds of formula (VI) respectively (VIa) respectively (VIb) with respect to the total weight of the mixture according to the aforementioned embodiments of the present invention is from 10 to 100 wt.-%, for example, 80 to 100 wt.-%, for example, 90 to 100 wt.-% and, for example, 95 to 100% wt. %.

The remainder to 100 wt.-%, if present, may, for example, comprise the respective ketals, unreacted compounds and their ketals, solvents or catalyst residues.

However, it was surprisingly found that during functionalization with compounds of formula E-H or E-Hal as described above, the respective ketals are reacted to form additional compounds of formula (VI) respectively (VIa) respectively (VIb) with the ethylene glycol released forming the respective mono and double esters, particularly double esters.

It was found that the compounds of formula (Ia) or mixtures comprising compounds of formula (IVa) may further be functionalized in an alternative way.

The present invention therefore further encompasses compounds of formula (VIIa)

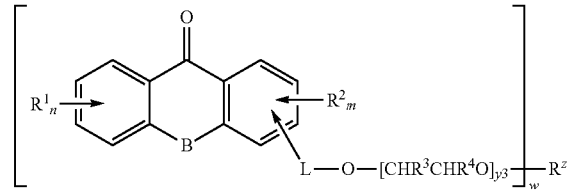

(VIIa)

wherein the arrows denote substitution at the aromatic ring without specifically indicating the relative position to the depicted keto-group if not mentioned otherwise hereinafter, and wherein B is either missing and the two aromatic rings are then therefore substituted with hydrogen, or where n or m are not zero alternatively also with $R^1$ or $R^2$ respectively, at the position where B is depicted to be bound at the aromatic ring, or is sulfur or oxygen, whereby B can, for example, be missing or sulfur, n is 0, 1 or 2, for example, 0 or 1 and, for example, 0, $R^1$ is independently of other substituents $R^1$ which may be present selected from the group consisting of hydrogen, $C_1$-$C_{18}$-alkyl, $C_2$-$C_{18}$-alkenyl, $C_1$-$C_{18}$-alkoxy, $C_1$-$C_{18}$-alkylthio, $C_6$-$C_{14}$-aryl, $C_6$-$C_{14}$-aryloxy, $C_6$-$C_{14}$-arylthio, —$N(R^5)_2$, fluoro, chloro and $COOR^5$, with $R^5$ being hydrogen or $C_1$-$C_{18}$-alkyl, m is 0, 1 or 2, for example, 0 or 1 and, for example, 0, $R^2$ is independently of other substituents $R^2$ which may be present selected from the group consisting of hydrogen, $C_1$-$C_{18}$-alkyl, $C_2$-$C_{18}$-alkenyl, $C_1$-$C_{18}$-alkoxy, $C_1$-$C_{18}$-alkylthio, $C_6$-$C_{14}$-aryl, $C_6$-$C_{14}$-aryloxy, $C_6$-$C_{14}$-arylthio, —$N(R^5)_2$, fluoro, chloro and $COOR^5$, with $R^5$ being hydrogen or $C_1$-$C_{18}$-alkyl, and wherein the substituent L-O[$CHR^3CHR^4O$]$_{y3}$— occupies the ortho-, meta or the para-position, for example, the ortho- or the para-position, and, for example, the para-position at the aromatic ring and with respect to the keto-function depicted in formula (VIIa), and wherein L is independently missing or a methylene group, i.e., Het is either directly bound to the aromatic ring or via a methylene group, $R^3$ and $R^4$ are either identically hydrogen or one of $R^3$ and $R^4$ is hydrogen and the other is methyl, whereby, $R^3$ and $R^4$ can, for example, be identically hydrogen, and y3 represents an integer of 1 or more, for example, of from 1 to 20, for example, of from 1 to 10 and, for example, 3 to 10, w is an integer of 2 or more, for example, 2, 3 or 4, and $R^z$ represents $R(CO)_x$ with R being an x-valent organic residue with 1 or more, for example, 1 to 30 carbon atoms.

Compounds of formula (VIIa) can, for example, be those wherein the arrows, B, $R^1$, n, $R^2$, m, $R^3$ and $R^4$ and L have the meaning set forth above for formula (VIa) and y3 has the same meaning as y2 in formula (VIa).

w is 2 and $R^z$ is a residue derived from terephthalic, phthalic, crotonic, itaconic, succinic, maleic or fumaric acid by abstraction of all OH-groups of the respective carboxylic functions.

The preparation of compounds of formula (VIIa) may be effected by standard esterification procedures known to those skilled in the art, which include, for example, and as an exemplary embodiment, contacting the compounds of formula (I) or mixtures of compounds of formula (IV) with acids R—$(COH)_x$ in the presence of an acid such as a mineral acid such as sulfuric or hydrochloric acid or a organic sulfonic acid such as p-toluene sulfonic acid, and removing water, for example, via distillation. Compounds of formula (I) or mixtures of compounds of formula (IV) can alternatively be treated with acid halides R—$(COHal)_x$, with Hal being Cl or Br, in the presence of a base such as an amine.

The present invention further encompasses mixtures comprising compounds of formula (VIIa), wherein, with respect to the number of repeating units y3, at least 50 wt.-%, for example, at least 55 wt.-% and, for example, at least 60 wt.-% of the total weight of compounds of formula (VIIa) within the mixture are those of formula (VIIa) having a number of repeating units y3 of 3 or more, for example, of 3 to 20, for example, 3 to 10 and, for example, 3, 4, 5, 6, 7 or 8 and, wherein none of the single compounds of formula (VIIa) is present in an amount of more than 50 wt.-% with respect to the total weight of compounds of formula (VIIa).

The weight of compounds of formula (VIIa) with respect to the total weight of the mixture according to the aforementioned embodiments of the present invention is from 10 to 100 wt.-%, for example, 80 to 100 wt.-%, for example, 90 to 100 wt.-% and, for example, 95 to 100% wt. %.

The remainder to 100 wt.-%, if present, may comprise, for example, the respective ketals, unreacted compounds, and their ketals, solvents or catalyst residues.

The compounds of formula (I), as well as the specified mixtures comprising compounds of formula (IV), the compounds of formula (VI), or mixtures thereof as specified above, or compounds of formula (VIIa) or mixtures thereof as specified above, are particularly useful as photoinitiators and for use in photo-curable compositions, in particular coating compositions, including varnishes, lacquers and printing inks, wood coatings, furniture coating, floor coatings, UV curable adhesives and UV curable resins as well as in other drying or curing compositions such as water-borne or solvent containing UV-curable formulations.

They are further useful as photoinitiators in heterophase polymerizations such as emulsion polymerizations.

The present invention therefore also relates to photo-curable compositions comprising (a) at least one ethylenically unsaturated component, and (b) at least one compound of formula (I), or a mixture comprising compounds of formula (IV) as specified above, or at least one compound of formula (VI) or mixtures thereof as specified above, or at least one compound of formula (VIIa) or mixtures thereof as specified above.

Where mixtures of compounds of formula (VI) are present, the term ethylenically unsaturated compound can, for example, denote a compound other than a compound of formula (VI).

Suitable ethylenically unsaturated components include mono(meth)acrylates, aliphatic or aromatic urethane (meth) acrylates, polyether (meth)acrylates, polyester (meth)acrylates and epoxy (meth)acrylates (such as bisphenol A epoxy acrylate).

Examples of suitable mono(meth)acrylates include methylacrylate, methyl methacrylate, ethyl acrylate, ethyl methacrylate, ethylhexyl acrylate, ethylhexyl methacrylate, hydroxyethyl acrylate, hydroxyethyl methacrylate, isobornyl acrylate, isobornyl methacrylate, butyl acrylate and butyl methacrylate.

Polyester (meth)acrylates include dipropylene glycol diacrylate, pentaerytritol tetraacrylate, di-pentaerytrityl hexaacrylate, di-, tri- and tetra-ethylenglycol diacrylate, hexanediol diacrylate, trimethylolpropane triacrylate, di-trimethylolpropane tetra-acrylate, di-pentaerythritol pentaacrylate.

Polyether acrylates include ethoxylated trimethylol propane triacrylate, glycerol propoxylate triacrylate, ethoxylated pentaerythritol tetraacrylate.

Epoxy acrylates include dianol diacrylate (=the diacrylate of 2, 2-bis [4-(2-hydroxyethoxy) phenyl] propane, e.g., Ebecryl 150 from UCB) and glycol diacrylates such as tripropylene glycol diacrylate, epoxidized soy bean oil acrylate.

The photo-curable compositions can, for example, contain at least one synergist.

Suitable synergists include but are not limited to 2-ethylhexyl-4-dimethylamino benzoate, ethyl 4-(dimethylamine) benzoate, N-methyl diethanolamine, 2-dimethylamino ethylbenzoate, butoxyethyl-4-dimethylamino benzoate, as well as C373, CN383, CN384, CN386 and CN 371, all available from Sartomer; Ebecryl P104, Ebecryl P115, Ebecryl 7100, all available from Allnex; and Roskydal UA XP 2299, available from Bayer, or the acrylated synergists such as Genomer 5142 and Genomer 5161, available from Rahn.

Further components which may be additionally present in the photo-curable compositions are:

isocyanates and/or polyisocyanates, flattening agents, matting agents,
defoamer,
anti-friction agents such as silicon containing antifriction agents,
surfactants,
resins such as formaldehyde resins, polyurethan resins, polyacrylates, cellulosic resins and sucrose benzoate,
further photoinitiators, including but not limited to, Norrish Type I initiators such as 2-hydroxy-1-{4-[4-(2-hydroxy-2-methyl-propionyl)-benzyl]-phenyl}-2-methyl-propan-1-one (Irgacure 127), 2-hydroxy-1-[4-(2-hydroxyethoxy)-phenyl]-phenyl]-2-methylpropan-1-one (Irgacure 2959), 1-hydroxy-cyclohexyl-phenyl-ketone (Irgacure 184), 2-hydroxy-2-methyl-1-phenyl-1-propanone (Irgacure 1173), benzildimethylketal and oligo[2-hydroxy-2-methyl-1-[4-(1-methylvinyl)phenyl]propanone] (Esacure KIP 150 from Lamberti) as well as mono- or bisacylphosphinoxides such as phenyl-bis(2,4,6-trimethylbenzoyl)phosphine oxide, diphenyl-(2,4,6-trimethylbenzoyl)phosphine oxide and ethyl-(2,4,6-trimethylbenzoyl)phenyl phosphinate.

Although the compounds of the present invention are especially useful as photoinitiators for use in the production of varnishes, they may also be used with advantage in many other kinds of energy-curable coating compositions. For example, although yellowing is not such a problem with printing inks, it may still be advantageous to have a photoinitiator which does not result in yellowing upon curing or upon aging, since this gives the ink formulator a much greater degree of freedom in choosing the other ingredients of the ink, including the pigment.

The amounts of ethylenically unsaturated components, photoinitiators, and optional other ingredients will vary according to the type of composition, the particular equipment to be used to apply it, and the application.

However, the amount of photoinitiator within the composition is typically in the range of from 0.5 to 12 wt.-%, for example, 2 to 10 wt.-%, for example, 4 to 9 wt.-%.

The compounds of formula (I) or the mixtures comprising compounds of formula (IV) are of particular advantage where isocyanates and/or polyisocyanates are intended to be used as further component since they are capable of reacting therewith.

A further aspect of the present invention therefore relates to compounds obtainable by reaction of compounds of formula (I) or mixtures comprising compounds of formula (IV) with isocyanates and/or polyisocyanates.

As used herein, the term polyisocyanates encompasses polyisocyanates comprising isocyanurate groups, uretdion-diisocyanates, polyisocyanates comprising biuret groups, polyisocyanates comprising urethane and/or allophanate groups, polyisocyanates comprising oxadiazintrione groups.

Specific examples of isocyanates and polyisocyanates include compounds of formulae (Va), (Vb) and (Vc),

$$OCN-R^5-NCO \quad (Va)$$

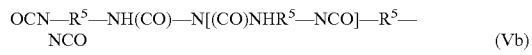

$$OCN-R^5-NH(CO)-N[(CO)NHR^5-NCO]-R^5-NCO \quad (Vb)$$

$$[OCN-R^5-N(CO)]_3 \quad (Vc),$$

wherein,
$R^5$ is a divalent hydrocarbon group having from 1 to 20 carbon atoms, for example, 2 to 13 carbon atoms, and in an exemplary embodiment 6 carbon atoms such as 1,6-hexanediyl or 13 carbon atoms such as 4,4'-dicyclohexylmethyl.

In an embodiment of the present invention, the compounds of formula (I) or the specific mixtures comprising compounds of formula (IV) as specified above or the mixture obtainable by the process according to the present invention may directly be reacted within the photo-curable composition, thus omitting a separate reaction and isolation or workup step. The ethylenically unsaturated compounds such as acrylates may simultaneously serve as a diluent and as a component of the photo-curable composition. The present invention further relates to a process for preparing a cured composition by exposing the photo-curable compositions according to the present invention to electromagnetic radiation, for example, ultraviolet radiation.

Suitable sources of electromagnetic radiation UV lamps like low-pressure, medium-pressure, high-pressure, and super-high-pressure mercury lamps which can be undoped or doped, e.g., with gallium iodide, thallium iodide or other metal halides; blue, violet-blue or UV-LEDs; concentrated, direct or indirect sunlight; xenon or xenon mercury arc lamps such as continuous-output xenon short- or long-arc lamps, flash lamps such as xenon or xenon mercury flash lamps; microwave-excited metal vapour lamps; excimer lamps, superactinic fluorescent tubes; fluorescent lamps; and noble gas incandescent lamps.

Sources include, for example, UV lamps such as low-pressure, medium-pressure, high-pressure, and super-high-pressure mercury lamps which can be undoped or doped, e.g., with gallium iodide, thallium iodide or other metal halides; blue, violet-blue or UV-LEDs, xenon or xenon mercury arc lamps such as continuous-output xenon short- or long-arc lamps.

Specific examples include H—UV lamps from Komori and LE-UV lamps from IST.

The cured compositions may be produced by all printing methods known to those skilled in the art including flexography, rotagravure, roller printing, screen printing, and ink jet, whereby the printed materials include paper, board, paperboard, plastic films and articles, e.g., from polypropylene, polyethylene, polyethyleneterephthalate, polyvinylchloride, polystyrene, aluminium, wood, laminate, tin or other metals, multi-layer substartes, or mixtures thereof, The printed materials are particular useful to be applied in articles comprising the printed materials, e.g., fine arts, pictures, newspapers, magazines, packaging, in particular packaging for food, tobacco and tobacco products, cosmetics, pharmaceuticals and the like.

The photo-curable compositions may also be used in other fields where UV-curing technologies are applied, such as other coating techniques like roller coating, curtain coating, spray coating, 3-D printing, molding compounds and the like.

The present invention therefore encompasses printed materials comprising the cured compositions according to the present invention and articles comprising said printed materials.

The advantage of the present invention is that the compounds provided based on readily available compounds of formula (II) as starting materials meet the high solubility in coating formulations, especially UV-curable formulations, very good reactivity, and in some cases significantly higher reactivity than some of the commonly used benzophenone derivatives commercially available today. The claimed photoinitiators are easy processible since liquid and available via a versatile and efficient process. They further exhibit a much lower tendency to migrate and be extracted than most benzophenone derivatives, in particular when reacted with other components of classical photo-curable compositions.

The present invention is hereinafter explained further via the examples without being limited thereto.

EXPERIMENTAL SECTION

Example 1

In a reactor, 1,000 kg [5.05 mol] of 4-hydroxybenzophenone were placed in a reaction vessel and 600 wt.-ppm KOH based on 4-hydroxybenzophenone were added. The reaction chamber was flushed with nitrogen. The mixture was reacted with 3.5 molar equivalents of ethylene oxide at temperatures of 130 to 150° C. for 5 hours at pressures of maximum 0.6 MPa.

The crude reaction mixture was analyzed by GC. The composition of the reaction mixture obtained thereby is listed in Table 1.

TABLE 1

| Ethylene oxide repeating units (s, q) f (free ketone) k (ketal) | % of total peak area | Wt.-% calculated (%-peak area* molar mass/ (Sum (peak area * molar mass) * 100) |
|---|---|---|
| 0 (k) | 0.12 | 0.09 |
| 1 (f) | 0.72 | 0.52 |
| 1 (k) | 1.80 | 1.53 |
| 2 (f) | 22.30 | 18.95 |
| 2 (k) | 2.20 | 2.16 |
| 3 (f) | 39.17 | 38.40 |
| 3 (k) | 1.14 | 1.27 |
| 4 (f) | 25.37 | 28.19 |
| 5 (f) | 7.18 | 8.92 |
| Sum | 100.00 | 100 |

*noise calibrated

The amount of compounds of formula (I, IV) (3≤q≤5) was 75.51 wt.-%. Further compounds of formula (I, IV) could be detected having up to 10 EO units, however, their combined intensities were lower than 2 wt.-% based on the sum (100 wt.-%) of compounds indicated in Table 1. Compounds having more than 10 EO units were not detected. None of the single compounds of formula (I, IV) had a share of 50 wt.-% or more. The amount of compounds of formula (I, IV) in the mixture of compounds of formula (I, IV) was above 90 wt.-%. The amount of compounds of formula (I,IV) with any t being 5 or more (q≥5) was less than 11 wt.-%.

The product appeared as a yellowish liquid having a viscosity of 2.5 Pa*s at 23° C. as measured by Thermo HAAKE Rheostress RS1.

An analogous reaction with propylene oxide resulted in a mixture of very similar composition having a viscosity of 1.86 Pa*s.

Both products showed superior processability and long term stability when employed in photocurable compositions.

The 4-benzophenonecarboxylic esters disclosed in EP 2 394 676 A1 and commercially available under the tradename Genopol* BP exhibits a viscosity of around 100 Pa*s.

Another product commercially available under the tradename Omnipol exhibits a viscosity of 200 Pa*s.

Example 2

In order to decompose the ketals, 1 g of the mixture obtained according to Example 1 was dissolved in 50 ml tetrahydrofurane:water 1:1 (v/v) and stirred for 24 h at room temperature after addition of 50 mg para-toluene sulfonic acid.

After addition of 100 ml of toluene, the organic phase was separated, washed with brine, dried with magnesium sulfate, and the solvent evaporated. No acetals could be detected by GC any more.

Example 3

20 grams (about 58 mmol) of the crude reaction mixture of Example 1 and 0.1 g of DABCO (1,4-diazabicyclo[2.2.2]octane) were dissolved in 10 g of propoxylated glycerol triacrylate (OTA 480, Cytec). 7.8 g H12MDI (4,4'-Diisocyanatodicyclohexylmethane) were added and the reaction temperature controlled at 60° C. for about 6 h. The reaction product obtained was obtained as a highly viscous, pale brown liquid.

Example 4

20 g (about 58 mmol) of the mixture obtained according to Example 1 and 8.4 g (92 mmol) acryloylchloride were dissolved in 120 mL tetrahydrofurane (THF) at room temperature. 9.37 g (93 mmol) of triethylamine were added dropwise over a period of 5 h.

The mixture was neutralized by adding 5 mL HCl (35% in $H_2O$) and 200 mL water were added. After separating the layers, the organic phase was washed with 3 times with saturated NaCl solution, dried with $MgSO_4$ and the solvent was evaporated under reduced pressure.

The originally present respective ketals were found to fully react to form the respective non-ketalized acyloylesters, while the ethylene glycol released formed the respective ethylene glycol diacrylate.

Yield: 92% of theory.

The mixture obtained showed neglectable signals of non-acrylated substance in MALDI-TOF measurements. The viscosity of the mixture was found to be even lower than the viscosity of the starting material (1.17 Pa*s at 23° C.).

Example 5

68 g (202 mmol) of the mixture obtained according to Example 1 was dissolved in 400 mL tetrahydrofurane (THF), and 22 g (108 mmol) terephtaloyl chloride were added under stirring. 25 g (247 mmol) triethylamine were dissolved separately in 70 mL THF and the solution was added dropwise to the reaction mixture over a period of 3 h and the mixture was further stirred for 4 h. 700 mL of distilled water and 20 mL of HCl (35%) were added to the mixture. After separating the layers, the organic phase was washed 3 times with saturated NaCl solution, dried with $MgSO_4$, and the solvent was evaporated under reduced pressure.

Yield: 90% of theory.

The IR spectrum did not show any broad OH-signal anymore at 3464 cm$^{-1}$ indicating complete conversion. A strong signal for the ester resonance at 1716 cm$^{-1}$ was detected.

Example 6—Reactivity Comparison

The reactivity of the mixture obtained according to Example 1 was tested in equal wt.-amounts versus Omnipol BP and Genopol* BP and other benzophenones.

The tested varnish was formulated as follows:

Genomer 5161 (Rahn AG) 9.21 parts, OTA-480 (Allnex) 55.25 parts; Miramer M300 (Rahn AG) 27.62 parts, Irgacure 127 (BASF) 0.92 parts, Tego Rad 2011 (Evonik Industries) 0.46 parts; Photoinitiator (Example 1 or Omnipol BP or Genopol* BP) 6.54 parts.

For comparison with low molecular weight benzophenone-derivatives, only 4 parts were used to reflect comparison of actual chromophore concentration.

Parts refer to parts by weight.

The mixture according to Example 1 showed superior behavior in mixing and homogenizing compared to the more viscuous Omnipol BP and Genopol* BP.

On a black printed carton, the varnish was applied in about 4 g/m$^2$ and passed under a UV Hg-lamp 200 W/cm, 50% in tensity) at 80 m/min. several times. The curing was determined by applying fine talcum powder on the surface and carefully wiping it off. The sample was fully cured when no talcum powder sticked to the surface. The number of passes for each varnish is set forth in Table 2.

TABLE 2

| Varnish | Number of passes until fully cured |
| --- | --- |
| Varnish with Genopol BP | 6 |
| Varnish with Omnipol BP | 4 |
| Varnish with Mixture of Example 1 | 4 |
| Varnish with 4-Hydroxybenzophenone | 7 |

Example 7—Leaching Behavior

Varnishes comprising of same components as in Example 6 with Omnipol BP, Genopol* BP, the mixtures of Example 1, and in two further runs, the mixtures of Examples 3 and 4, were each applied with 10 g/m$^2$ on a polyester foil and passed under a standard mercury lamp (200 W/cm) with 20 m/min. 1 dm$^2$ of the sample was extracted with ethanol (95 vol.-%) for 24 h at room temperature, and the extracted amount of photoinitiator was determined accordingly. The following leaching rates were found:

Genopol* BP: 50 μg/dm$^2$

Omnipol BP: 39 μg/dm$^2$

Mixture of Example 1*: 1445 μg/dm$^2$

Mixture of Example 3*: 37 μg/dm$^2$

Mixture of Example 4**: 10 μg/dm$^2$

*measured amount of compounds of Example 1)
**measured amount of compounds of Example 4).

Example 4 was detected in significant lower amounts than compared to all other tested photoinitiators despite having a comparably low molecular weight which indicates superior usability in application such as food packaging were low leaching levels are more than desirable.

Example 8

In a reactor, 20 g [88 mmol] of 2-hydroxythioxanthen-9-one were placed in a reaction vessel and 600 wt.-ppm KOH (based on 2-hydroxythioxanthen-9-one) were added together with 100 g isoaliphatic naphta. The reaction chamber was flushed with nitrogen. The mixture was reacted with 3.5 molar equivalents of ethylene oxide at temperatures of 130 to 150° C. for 3 h at pressures of max. 0.6 MPa.

The crude reaction mixture was analyzed by MALDI-TOF:

TABLE 3

| Ethylene oxide repeating units | % of rel. intensities | Ethylene oxide repeating units | % of total rel. intensities |
| --- | --- | --- | --- |
| 2 | 2.3 | 7 | 13.0 |
| 3 | 10.7 | 8 | 7.9 |
| 4 | 19.7 | 9 | 2.9 |
| 5 | 23.7 | 10 | 0.8 |
| 6 | 19.9 | | |

Mn=460 was calculated based on the mass count distribution

The present invention is not limited to embodiments described herein; reference should be had to the appended claims.

What is claimed is:

1. Mixtures comprising compounds of formula (IV):

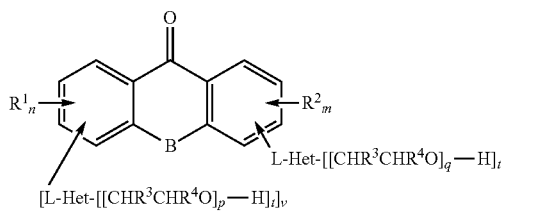

(IV)

wherein the arrows denote substitution at the aromatic ring without specifically indicating the relative position to the depicted keto-group if not otherwise mentioned, B is either missing so that the two aromatic rings are substituted with a hydrogen, or where n or m are not zero, with either R$^1$ or R$^2$ at the position where B is depicted to be bound at the aromatic ring, or is sulfur or oxygen, n is 0, 1 or 2, R$^1$ is selected from the group consisting of C$_1$-C$_{18}$-alkyl, C$_2$-C$_{18}$-alkenyl, C$_1$-C$_{18}$-alkoxy, C$_1$-C$_{18}$-alkylthio, C$_6$-C$_{14}$-aryl, C$_6$-C$_{14}$-aryloxy, C$_6$-C$_{14}$-arylthio, —N(R$^5$)$_2$, fluoro, chloro and COOR$^5$ with R$^5$ being hydrogen or C$_1$-C$_{18}$-alkyl, m is 0, 1 or 2, R$^2$ is selected from the group consisting of C$_1$-C$_{18}$-alkyl, C$_2$-C$_{18}$-alkenyl, C$_1$-C$_{18}$-alkoxy, C$_1$-C$_{18}$-alkylthio, C$_6$-C$_{14}$-aryl, C$_6$-C$_{14}$-aryloxy, C$_6$-C$_{14}$-arylthio, —N(R$^5$)$_2$, fluoro, chloro and COOR$^5$, with R$^5$ being hydrogen or C$_1$-C$_{18}$-alkyl, and v is 0 or 1, the substituents L-Het[[CHR$^3$CHR$^4$O]$_p$—H]$_t$, if present, and L-Het-[CHR$^3$CHR$^4$O]$_q$—H]$_t$ independently of each other occupy the ortho-, meta or the para-position at their respective aromatic ring and with respect to the keto-function depicted in formula (IV), and wherein, L is independently missing or is a methylene group so that Het is either directly bound to the aromatic ring or via a methylene group, Het is independently sulphur, oxygen, N(C$_1$-C$_{18}$-Alkyl), or N, t is 1 for Het=sulphur, oxygen, N(C$_1$-C$_{18}$-Alkyl), and is 2 for for Het=N, $R^3$ and $R^4$ are either identically hydrogen or one of $R^3$ and $R^4$ is hydrogen and the other is methyl, and p and q independently of each other is an integer of 0 or more, wherein with respect to the number of repeating units p and q, at least 50 wt.-% of the total weight of the compounds of formula (IV) within the mixture are those of formula (IV), wherein q, where v is 0 and t is 1, or at least one of p and q, where both t are 1, or at least one of all q, where v=0 and t is 2, or at least one of all p and all q, where v=1 and where at least one t is 2, is 3 or more, wherein no single compound of formula (IV) is present in an amount of more than 50 wt.-% with respect to the total weight of the compounds of formula (IV) in the mixture, and wherein the total amount of compounds of formula (IV) present in the mixture comprising the compounds of formula (IV) having at least one of p and q being 5 or larger is 20 wt.-% or less.

2. The mixture as recited in claim 1, wherein no single compound of formula (IV) is present in an amount of more than 45 wt.-% with respect to the total weight of the compounds of formula (IV) in the mixture.

3. The mixture as recited in claim 1, wherein the weight of the compounds of formula (IV) with respect to the total weight of the mixture is from 10 to 100 wt.-%.

4. The mixture as recited in claim 1, wherein the compounds of formula (IV) are those of formula (IVa):

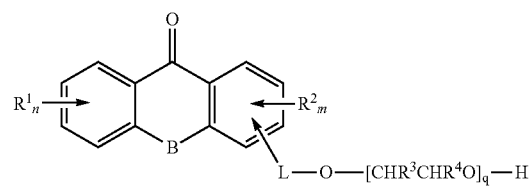

(IVa)

wherein the arrows, B, n, $R^1$, m, $R^2$, $R^3$, $R^4$ and L have the same meaning as set forth for formula (IV), and q is an integer of 0 or more, wherein, with respect to the number of repeating units q, at least 50 wt.-% of the total weight of the compounds of formula (IVa) within the mixture are those of formula (IVa) having a number of repeating units q of 3 or more, wherein no single compound of formula (IVa) is present in an amount of more than 50 wt.-% with respect to the total weight of compounds of formula (IVa), and wherein the total amount of compounds of formula (IVa) present in the mixture comprising the compounds of formula (IVa) having at least one of p and q being 5 or larger is 20 wt.-% or less.

5. The mixture as recited in claim 1, wherein the compounds of formula (IV) are those of formula (IVb):

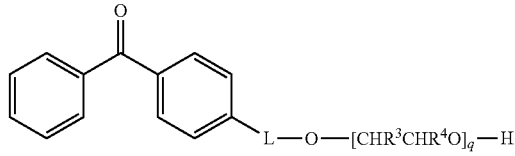

(IVb)

wherein L, $R^3$ and $R^4$ have the meaning as set forth for formula (IV), and q is an integer of 0 or more, wherein, with respect to the number of repeating units q, at least 50 wt.-% of the total weight of the compounds of formula (IVb) within the mixture are those of formula (IVb) having a number of repeating units q of 3 or more, wherein no single compound of formula (IVb) is present in an amount of more than 50 wt.-% with respect to the total weight of compounds of formula (IVb), and wherein the total amount of compounds of formula (IVb) present in the mixture comprising the compounds of formula (IVb) having at least one of p and q being 5 or larger is 20 wt.-% or less.

6. The mixture as recited in claim 1, wherein L is missing.

7. Mixtures of compounds of formula (VI):

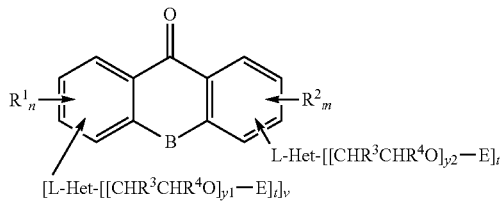

(VI)

wherein, the arrows denote substitution at the aromatic ring without specifically indicating a relative position to the depicted keto-group if not mentioned otherwise, B is either missing so that the two aromatic rings are substituted with a hydrogen, or where n or m are not zero, with either $R^1$ or $R^2$ at the position where B is depicted to be bound at the aromatic ring, or is sulfur or oxygen, n is 0, 1 or 2, $R^1$ is selected from the group consisting of hydrogen, $C_1$-$C_{18}$-alkyl, $C_2$-$C_{18}$-alkenyl, $C_1$-$C_{18}$-alkoxy, $C_1$-$C_{18}$-alkylthio $C_6$-$C_{14}$-aryl, $C_6$-$C_{14}$-aryloxy, $C_6$-$C_{14}$-arylthio, $-N(R^5)_2$, fluoro, chloro and $COOR^5$ with $R^5$ being hydrogen or $C_1$-$C_{18}$-alkyl, m is 0, 1 or 2, $R^2$ is selected from the group consisting of hydrogen, $C_1$-$C_{18}$-alkyl, $C_2$-$C_{18}$-alkenyl, $C_1$-$C_{18}$-alkoxy, $C_1$-$C_{18}$-alkylthio, $C_6$-$C_{14}$-aryl, $C_6$-$C_{14}$-aryloxy, $C_6$-$C_{14}$-arylthio, $-N(R^5)_2$, fluoro, chloro and $COOR^5$, with $R^5$ being hydrogen or $C_1$-$C_{18}$-alkyl, and wherein v is 0 or 1, the substituents L-Het-[[$CHR^3CHR^4O$]$_{y1}$-E], where present, and L-Het-[[$CHR^3CHR^4O$]$_{y2}$-E]independently of each other occupy the ortho-, meta or the para-position at their respective aromatic ring and with respect to the keto-function depicted in formula (I), and
wherein
L is independently missing or is a methylene group so that Het is either directly bound to the aromatic ring or via a methylene group,
Het is independently sulphur, oxygen, N($C_1$-$C_{18}$-Alkyl), NH or N,
t is 1 for Het=sulphur, oxygen, N($C_1$-$C_{18}$-Alkyl), NH, and is 2 for for Het=N,
$R^3$ and $R^4$ are either identically hydrogen or one of $R^3$ and $R^4$ is hydrogen and the other is methyl, and
if t is 1,
y1 and y2 independently of each other is an integer of 0 or more,
whereby,
the sum of y1 and y2 is at least 1 for v=1, or
y2 is at least 1where v=0,
if t is 2,
all y1 and y2 independently of each other is an integer of 0 or more, whereby
the sum of all y1 and all y2 is at least 1 for v=1, or
the sum of all y2 is at least 1 where v=0,
and
E independently identically is $H_2C$=CH—CO—, ($CH_3$)HC=CH—CO— or $H_2C$=C($CH_3$)—CO—,
wherein with respect to the number of repeating units y1 and y2 are at least 50 wt.-% of the total weight of the compounds of formula (VI) within the mixture, wherein
y2, where v is 0 and t is 1, or
at least one of y1 and y2, where both t are 1, or
at least one of all y2, where v=0 and t is 2, or
at least one of all y1 and all y2, where v=1 and where at least one t is 2,
is 3 or more,
wherein no single compound of formula (VI) is present in an amount of more than 50 wt.-% with respect to the total weight of the compounds of formula (VI), and
wherein the total amount of compounds of formula (Vi) present in the mixture comprising the compounds of formula (VI) having at least one of p and q being 5 or larger is 20 wt.-% or less.

8. The mixture as recited in claim 7, wherein no single compound of formula (VI) is present in the amount of more than 45 wt.-% with respect to the total weight of compounds of formula (VI).

9. The mixture as recited in claim 7, wherein the compounds of formula (VI) are those of formula (VIa):

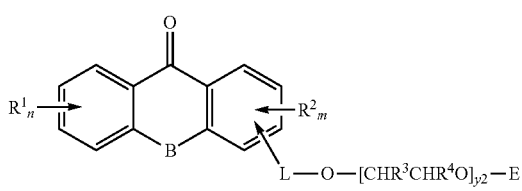

(VIa)

wherein the arrows, B, $R^1$, n, $R^2$, m, L, $R^3$, $R^4$ and E have the meaning set forth for formula (VI) and y2 is an integer of 1 or more,
wherein with respect to the number of repeating units y2,
at least 50 wt.-% of the total weight of compounds of formula (VIa) within the mixture are those of formula (VIa) having a number of repeating units y2 of 3 or more,
wherein no single compound of formula (VIa) is present in an amount of more than 50 wt.-% with respect to the total weight of the compounds of formula (VIa), and
wherein the total amount of compounds of formula (VIa) present in the mixture comprising the compounds of formula (VIa) having at least one of p and q being 5 or larger is 20 wt.-% or less.

10. The mixtures as recited in claim 7, wherein the compounds of formula (VI) are compounds of formula (VIb):

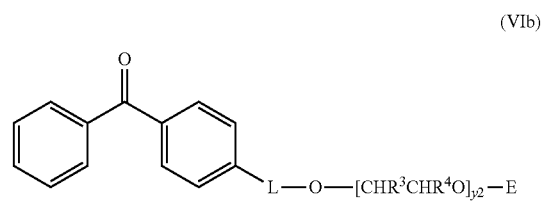

(VIb)

wherein L, $R^3$, $R^4$ and E have the meaning set forth for formula (VI) and y2 is an integer of 1 or more,
wherein with respect to the number of repeating units y2,
at least 50 wt.-% of the total weight of compounds of formula (VIb) within the mixture are those of formula (VIb) having a number of repeating units y2 of 3 or more,
wherein no single compound of formula (VIb) is present in an amount of more than 50 wt.-% with respect to the total weight of the compounds of formula (VIb), and
wherein the total amount of compounds of formula (VIb) present in the mixture comprising the compounds of formula (VIb) having at least one of p and q being 5 or larger is 20 wt.-% or less.

11. A photo-curable composition, comprising
(a) at least one ethylenically unsaturated component; and
(b) at least a mixture comprising:
compounds of formula (IV):

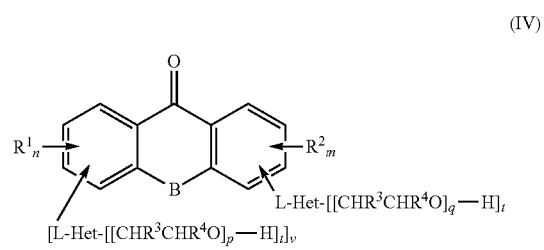

(IV)

wherein
the arrows denote substitution at the aromatic ring without specifically indicating the relative position to the depicted keto-group if not otherwise mentioned,
B is either missing so that the two aromatic rings are substituted with a hydrogen, or where n or m are not zero, with either $R^1$ or $R^2$ at the position where B is depicted to be bound at the aromatic ring, or is sulfur or oxygen,
whereby B is preferably missing or sulfur and more preferably B is missing n is 0, 1 or 2, $R^1$ is selected from the group consisting of $C_1$-$C_{18}$-alkyl, $C_2$-$C_{18}$-alkenyl, $C_1$-$C_{18}$-alkoxy, $C_1$-$C_{18}$-alkylthio $C_6$-$C_{14}$-aryl, $C_6$-$C_{14}$-aryloxy, $C_6$-$C_{14}$-arylthio, —N($R^5$)$_2$, fluoro, chloro and COO$R^5$ with $R^5$ being hydrogen or $C_1$-$C_{18}$-alkyl, m is 0, 1 or 2, $R^2$ is selected from the group consisting of $C_1$-$C_{18}$-alkyl, $C_2$-$C_{18}$-alkenyl, $C_1$-$C_{18}$-alkoxy, $C_1$-$C_{18}$-alkylthio, $C_6$-$C_{14}$-aryl, $C_6$-$C_{14}$-aryloxy, $C_6$-$C_{14}$-arylthio, —N($R^5$)$_2$, fluoro, chloro and COO$R^5$, with $R^5$ being hydrogen or $C_1$-$C_{18}$-alkyl, and v is 0 or 1, the substituents L-Het[[CHR$^3$CHR$^4$O]$_p$—H]$_t$, if present, and L-Het-[CHR$^3$CHR$^4$O]$_q$—H]$_t$ independently of each other occupy the ortho-, meta or the para-position at their respective aromatic ring and with respect to the keto-function depicted in formula (IV), and wherein, L is independently missing or is a methylene group so that Het is either directly bound to the aromatic ring or via a methylene group, Het is independently sulphur, oxygen, N($C_1$-$C_{18}$-Alkyl), or N, t is 1 for Het=sulphur, oxygen, N($C_1$-$C_{18}$-Alkyl), and is 2 for for Het=N, $R^3$ and $R^4$ are either identically hydrogen or one of $R^3$ and $R^4$ is hydrogen and the other is methyl, and p and q independently of each other is an integer of 0 or more, wherein with respect to the number of repeating units p and q, at least 50 wt.-% of the total weight of the compounds of formula (IV) within the mixture are those of formula (IV), wherein q, where v is 0 and t is 1, or at least one of p and q, where both t are 1, or at least one of all q, where v=0 and t is 2, or at least one of all p and all q, where v=11 and where at least one t is 2, is 3 or more, wherein no single compound of formula (IV) is present in an amount of more than 50 wt.-% with respect to the total weight of the compounds of formula (IV) in the mixture, and wherein the total amount of compounds of formula (IV) present in the mixture comprising the compounds of formula (IV) having at least one of p and q being 5 or larger is 20 wt.-% or less, or compounds of formula (VI):

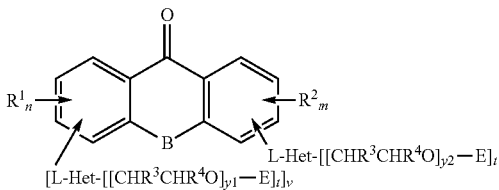

(VI)

wherein, the arrows denote substitution at the aromatic ring without specifically indicating a relative position to the depicted keto-group if not mentioned otherwise, B is either missing so that the two aromatic rings are substituted with a hydrogen, or where n or m are not zero, with either $R^1$ or $R^2$ at the position where B is depicted to be bound at the aromatic ring, or is sulfur or oxygen, n is 0, 1 or 2, $R^1$ is selected from the group consisting of hydrogen, $C_1$-$C_{18}$-alkyl, $C_2$-$C_{18}$-alkenyl, $C_1$-$C_{18}$-alkoxy, $C_1$-$C_{18}$-alkylthio $C_6$-$C_{14}$-aryl, $C_6$-$C_{14}$-aryloxy, $C_6$-$C_{14}$-arylthio, —N($R^5$)$_2$, fluoro, chloro and COO$R^5$ with $R^5$ being hydrogen or $C_1$-$C_{18}$-alkyl, m is 0, 1 or 2, $R^2$ is selected from the group consisting of hydrogen, $C_1$-$C_{18}$-alkyl, $C_2$-$C_{18}$-alkenyl, $C_1$-$C_{18}$-alkoxy, $C_1$-$C_{18}$-alkylthio, $C_6$-$C_{14}$-aryl, $C_6$-$C_{14}$-aryloxy, $C_6$-$C_{14}$-arylthio, —N($R^5$)$_2$, fluoro, chloro and COO$R^5$, with $R^5$ being hydrogen or $C_1$-$C_{18}$-alkyl, and wherein v is 0 or 1, the substituents L-Het-[[CHR$^3$CHR$^4$O]$_{y1}$-E], where present, and L-Het-[[CHR$^3$CHR$^4$O]$_{y2}$-E]independently of each other occupy the ortho-, meta or the para-position at their respective aromatic ring and with respect to the keto-function depicted in formula (I), and wherein L is independently missing or is a methylene group so that Het is either directly bound to the aromatic ring or via a methylene group, Het is independently sulphur, oxygen, N($C_1$-$C_{18}$-Alkyl), NH or N, t is 1 for Het=sulphur, oxygen, N($C_1$-$C_{18}$-Alkyl), NH, and is 2 for for Het=N, $R^3$ and $R^4$ are either identically hydrogen or one of $R^3$ and $R^4$ is hydrogen and the other is methyl, and if t is 1, y1 and y2 independently of each other is an integer of 0 or more, whereby, the sum of y1 and y2 is at least 1 for v=1, or y2 is at least 1 where v=0, if t is 2, all y1 and y2 independently of each other is an integer of 0 or more, whereby the sum of all y1 and all y2 is at least 1 for v=1, or the sum of all y2 is at least 1 where v=0, and E independently identically is H$_2$C=CH—CO—, (CH$_3$)HC=CH—CO— or H$_2$C=C(CH$_3$)—CO—, wherein with respect to the number of repeating units y1 and y2 are at least 50 wt.-% of the total weight of the compounds of formula (VI) within the mixture, wherein y2, where v is 0 and t is 1, or at least one of y1 and y2, where both t are 1, or at least one of all y2, where v=O0 and t is 2, or at least one of all y1 and all y2, where v=11 and where at least one t is, 2 is 3 or more, and wherein no single compound of formula (VI) is present in an amount of more than 50 wt.-% with respect to the total weight of compounds of formula (VI), and wherein the total amount of compounds of formula (IV) present in the mixture comprising the compounds of formula (IV) having at least one of p and q being 5 or larger is 20 wt.-% or less,
or
compounds of formula (VIIa):

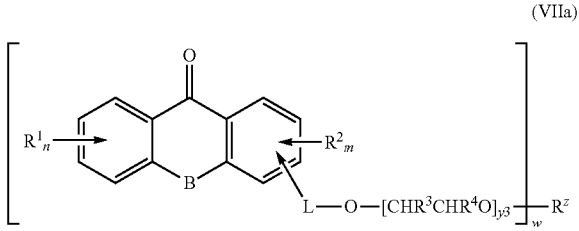

(VIIa)

wherein
the arrows denote substitution at the aromatic ring without specifically indicating a relative position to the depicted keto-group if not mentioned otherwise hereinafter,
B is either missing so that the two aromatic rings are substituted with a hydrogen, or where n or m are not zero, with either $R^1$ or $R^2$ at the position where B is depicted to be bound at the aromatic ring, or is sulfur or oxygen,
n is 0, 1 or 2,
$R^1$ is selected from the group consisting of hydrogen, $C_1$-$C_{18}$-alkyl, $C_2$-$C_{18}$-alkenyl, $C_1$-$C_{18}$-alkoxy, $C_1$-$C_{18}$-alkylthio $C_6$-$C_{14}$-aryl, $C_6$-$C_{14}$-aryloxy, $C_6$-$C_{14}$-arylthio, —N($R^5$)$_2$, fluoro, chloro and COOR$^5$ with $R^5$ being hydrogen or $C_1$-$C_{18}$-alkyl,
m is 0, 1 or 2,
$R^2$ is selected from the group consisting of hydrogen, $C_1$-$C_{18}$-alkyl, $C_2$-$C_{18}$-alkenyl, $C_1$-$C_{18}$-alkoxy, $C_1$-$C_{18}$-alkylthio, $C_6$-$C_{14}$-aryl, $C_6$-$C_{14}$-aryloxy, $C_6$-$C_{14}$-arylthio, —N($R^5$)$_2$O fluoro, chloro and COOR$^5$, with $R^5$ being hydrogen or $C_1$-$C_{18}$-alkyl, and
wherein
the substituent L-O[CHR$^3$CHR$^4$O]$_{y3}$— occupies the ortho-, meta or the para-position at the aromatic ring and with respect to the keto-function depicted in formula (VIIa), and
wherein
L is independently missing or a methylene group so that Het is either directly bound to the aromatic ring or via a methylene group, $R^3$ and $R^4$ are either identically hydrogen or one of $R^3$ and $R^4$ is hydrogen and the other is methyl, and
y3 is an integer of 1 or more,
w is an integer of 2 or more, and
$R^z$ is R(CO)$_x$ with R being an x-valent organic residue with 1 or more carbon atoms.

12. The photo-curable composition as recited in claim 11, wherein the at least one ethylenically unsaturated components is selected from mono(meth)acrylates, aliphatic or aromatic urethane (meth)acrylates, polyether (meth)acrylates, polyester (meth)acrylates and epoxy (meth)acrylates.

13. The photo-curable composition as recited in claim 12, wherein the mono(meth)acrylates are selected from the group consisting of methylacrylate, methyl methacrylate, ethyl acrylate, ethyl methacrylate, ethylhexyl acrylate, ethylhexyl methacrylate, hydroxyethyl acrylate, hydroxyethyl methacrylate, isobornyl acrylate, isobornyl methacrylate, butyl acrylate, and butyl methacrylate.

14. The photo-curable composition as recited in claim 12, wherein the polyester (meth)acrylates are selected from the group consisting of dipropylene glycol diacrylate, pentaerytritol tetraacrylate, di-pentaerytrityl hexaacrylate, di-, tri- and tetra-ethylenglycol diacrylate, hexanediol diacrylate, trimethylolpropane triacrylate, di-trimethylolpropane tetraacrylate, and di-pentaerythritol pentaacrylate.

15. The photo-curable composition as recited in claim 12, wherein the polyether (meth)acrylates are selected from the group consisting of ethoxylated trimethylol propane triacrylate, glycerol propoxylate triacrylate, and ethoxylated pentaerythritol tetraacrylate.

16. The photo-curable composition as recited in claim 12, wherein the epoxy (meth)acrylates are selected from the group consisting of dianol diacrylate (=the diacrylate of 2, 2-bis [4-(2-hydroxyethoxy) phenyl] propane, and glycol diacrylates, and epoxidized soy bean oil acrylate.

17. The photo-curable composition as recited in claim 11, further comprising:
at least one synergist.

18. The photo-curable composition as recited in claim 11, further comprising at least one component selected from:
isocyanates, polyisocyanates, flattening agents, matting agents, a defoamer, anti-friction agents, surfactants, resins, polyacrylates, cellulosic resins, sucrose benzoate, and further photoinitiators.

19. A cured composition obtainable by exposing the photo-curable composition as recited in claim 11 to electromagnetic radiation.

* * * * *